US 12,427,191 B1

United States Patent
Deisseroth

(10) Patent No.: US 12,427,191 B1
(45) Date of Patent: Sep. 30, 2025

(54) SARS-CoV-2 FUSION PROTEIN VACCINE/REGIMEN

(71) Applicant: MicroVAX, LLC, Warrenton, VA (US)

(72) Inventor: Albert B. Deisseroth, Potomac, MD (US)

(73) Assignee: MicroVAX, LLC, Warrenton, VA (US)

( * ) Notice: Subject to any disclaimer, the term of this patent is extended or adjusted under 35 U.S.C. 154(b) by 832 days.

(21) Appl. No.: 17/726,801

(22) Filed: Apr. 22, 2022

Related U.S. Application Data

(60) Provisional application No. 63/178,598, filed on Apr. 23, 2021.

(51) Int. Cl.
| | |
|---|---|
| *A61K 39/215* | (2006.01) |
| *A61K 9/00* | (2006.01) |
| *A61K 38/20* | (2006.01) |
| *A61K 39/395* | (2006.01) |
| *C07K 14/005* | (2006.01) |
| *C07K 14/705* | (2006.01) |
| *C12N 15/86* | (2006.01) |
| *A61K 39/00* | (2006.01) |

(52) U.S. Cl.
CPC .......... *A61K 39/215* (2013.01); *C07K 14/005* (2013.01); *C07K 14/70575* (2013.01); *A61K 2039/53* (2013.01); *A61K 2039/645* (2013.01); *A61K 2039/70* (2013.01); *C07K 2319/33* (2013.01); *C07K 2319/735* (2013.01); *C12N 2770/20022* (2013.01); *C12N 2770/20034* (2013.01)

(58) Field of Classification Search
CPC .............. C07K 14/005; C07K 2319/00; C07K 16/1002; C07K 16/1003; C07K 2317/33
See application file for complete search history.

(56) References Cited

PUBLICATIONS

Francica et al., "Vaccination with SARS-CoV-2 spike protein and AS03 adjuvant induces rapid anamnestic antibodies in the lung and protects against virus challenge in nonhuman primates", bioRxiv, Mar. 2021 preprint publicly available in PMC;pp. 1-42.*
Wrapp, D. et al., Cryo-EM structure of the 2019-nCoV spike in the prefusion conformation, Science, 367: 1260-1263, Mar. 13, 2020.
Lan, J. et al., Structure of the SARS-CoV-2 spike receptor binding domain bound to the ACE2 receptor, Nature, 581: 215-220, May 14, 2020.
Huang, Y. et al., Structural and functional properties of SARS-CoV-2 spike protein: potential antivirus drug development for COVID-19, Acta Pharmacological Sinica, 41: 1141-1149, Aug. 3, 2020.
Wang, C. et al., A human monoclonal antibody blocking SARS-CoV-2 Infection, Nature Communications, 11:2251, 6 pages, 2020.
Wang, Q. et al., Structural and functional basis of SARS-CoV-2 entry by using human ACE2, Cell, 181, 894-904, May 14, 2020.
Walls, A.C. et al., Structure, Function and Antigenicity of the SARS-CoV-2 Spike Glycoprotein, Cell, 180: 281-292, Apr. 16, 2020.
Hou, Y.J. et al., SARS-CoV-2 D614G variant exhibits efficient replication ex vivo and transmission in vivo, Science, 370: 1464-1468, Dec. 18, 2020.
Lasek-Nesselquist, E. et al., The localized rise of a B.1.526 SARS-CoV-2 variant containing an E484K mutation in NewYork State, Mar. 1, 2021, 12 pages.
Zhang, L. et al.. An adenoviral vector cancer vaccine that delivers a tumor-associated antigen/CD40-ligand fusion protein to dendritic cells, PNAS, 100(25): 15101-15106, Dec. 9, 2023.
Akbulut, H. et al., Vector Targeting Makes 5-Fluorouracil Chemotherapy Less Toxic and More Effective in Animal Models of Epithelial Neoplasms, Clinical Cancer Research, 10: 7738-7746, Nov. 15, 2004.
Tang, Y. et al., Multistep Process Through Which Adenoviral Vector Vaccine Overcomes Anergy to Tumor-associated Antigens, Blood, 104(9): 2704-2713 , Nov. 1, 2004.
Akbulut, H et al., Antitumor immune response induced by i.t. injection of vector activated dendritic cells and chemotherapy suppresses metastatic breast cancer, Molecular Cancer Ther., 5(8): 1975-1985, Aug. 2006.
Tang, Y.C. et al., Vector Prime/Protein Boost Vaccine That Overcomes Defects Acquired during Aging and Cancer, Journal of Immunology 177: 5697-5707, 2006.
Tang, Y. et al., Vaccine strategies for cancer and infectious diseases in the elderly, Gene Therapy, 2007, 11 pages.
Akbulut, H et al., Chemotherapy Targeted to Cancer Tissue Potentiates Antigen-specific Immune Response Induced by Vaccine for In Vivo Antigen Loading and Activation of Dendritic Cells, Molecular Therapy, 16(10) 1753-1760, Oct. 2008.
Tang, Y.C. et al., Symposium in Writing: Use of CD40L immunoconjugates to overcome the defective immune response to vaccines for infections and cancer in the aged, Cancer Immunology and Immunotherapy, 58: 1949-1957, May 15, 2009.

(Continued)

*Primary Examiner* — Barry A Chestnut
(74) *Attorney, Agent, or Firm* — Jacob Frank; Glenn Snyder

(57) ABSTRACT

A SARS-CoV-2 immunotherapeutic targeted fusion protein regimen or vaccine in which the extracellular domain (ecd) of the CD40L immunostimulatory protein, is attached individually to mRNA encoding a Selected Fragment of the Spike Protein (SFSP), representing a different functional feature and a different domain or domain region, or both of the Spike Protein, to generate 7 distinct SFSP/ecdCD40L translation units, each translation unit being converted into a SFSP/ecdCD40L fusion protein regimen or vaccine and all combined into a single fusion protein mixture or composition for injection, preferably inter-muscularly (im). Each fragment or peptide is designed to activate a humoral and cellular immune response to a different SFSP. Each SFSP fragment or peptide, as a vaccine strategy for the SARS-CoV-2 virus, has the capability to suppress the emergence of immunological escape mutants. The fusion protein mixture or composition of multiple fragments or peptides could be incorporated in any one of several delivery platforms such as an adenoviral expression vector or an mRNA platform.

15 Claims, 3 Drawing Sheets

Specification includes a Sequence Listing.

(56) References Cited

PUBLICATIONS

Han T.H. et al., Vector prime protein boost vaccination in the setting of myeloablative-induced lymphopenia suppresses growth of leukemia and solid tumors, Bone Marrow Transplantation, 45, 550-557, Aug. 2009.
Akbulut H. et al., Addition of adenoviral vector targeting of chemotherapy to the MUC-1/ecdCD40L VPPP vector prime protein boost vaccine prolongs survival of mice carrying growing subcutaneous deposits of Lewis lung cancer cells, Gene Therapy, 8 pages, Jul. 2010.
Deisseroth A. et al., TAA/ecdCD40L adenoviral prime-protein boost vaccine for cancer and infectious diseases, Cancer Gene Therapy, 5 pages, Nov. 11, 2012.
Wu F. et al., A new coronavirus associated with human respiratory disease in China, Nature, 579: 265-269, Mar. 12, 2020.
Xia S. et al., A pan-coronavirus fusion inhibitor targeting the HR1 domain of human coronavirus spike, Science Advances 5: eaav4580 (2019), 15 pages, Apr. 10, 2019.
Wang, P. et al., Antibody resistance of SARS-CoV-2 variants B.1.351 and B.1.1.7. Nature, 593: 130-135, May 6, 2021.
Sauer K and Harris T. An Effective COVID-19 Vaccine Needs to Engage T Cells, Frontiers in Immunology,11:1-6, Sep. 2020.
Dan J. et al., Immunological memory to SARS-CoV-2 assessed for up to 8 months after infection, Science, 371, 15 pages, Feb. 5, 2021.
Editorial: Understanding the long-term health effects of COVID-19. EClinicalMedicine 26, 2 pages, 2021.

* cited by examiner

SARS-CoV-2 FUSION PROTEIN VACCINE/REGIMEN

CROSS-REFERENCE TO RELATED APPLICATION

This application claims priority and the benefit under 35 U.S.C. § 119(e) to U.S. Provisional Application No. 63/178,598 filed Apr. 23, 2021, the disclosure of which is hereby incorporated by reference herein in its entirety.

BACKGROUND OF THE INVENTION

A novel coronavirus, 2019-nCoV, otherwise known as SARS-CoV-2, has been identified as the etiological agent of COVID-19, which is the name for the disease caused by the infection with the SARS-CoV-2 virus, has been declared a global pandemic by WHO (1-8). This virus has been found to be related to the SARS-CoV. An early coronavirus responsible for the 2002 epidemic of severe respiratory distress in 2002 (20). The SARS-CoV-2 virus appears to spread from human to human faster than was the case with the original SARS-CoV-2 virus (7,21).

The world economy has been held in the grip of the new coronavirus (SARS-CoV-2) causing a pandemic which has disrupted all aspects of life for 2020 and at least the first quarter of 2021 (1-8, 20-25). Infection with SARS-CoV-2 was associated with the short-term threat of respiratory failure and loss of life in certain high-risk groups (e.g. advanced chronological age, obesity, diabetes mellitus and hypertension), and the long-term risk of diminished organ function in the heart, lungs, liver, and central nervous system (25).

No sooner had the successful development of several commercial vaccine strategies, each associated with a protective antibody response in a high percentage of vaccinated individuals, brought hope for an end to the COVID-19 (the name for the infection caused for the SARS-CoV-2 virus) pandemic, than a variety of variant mutant strains of SARS-CoV-2 arose in multiple locations around the world (7-8, 22). Some of these mutant strains have been reported to be less sensitive to the effects of neutralizing antibodies (8,22) generated against SARS-CoV-2 suggesting the possibility that the pandemic might continue for several years to come in one form or another.

Structure of the Spike Protein (S) Protein of SARS-CoV-2 Virus

The S protein of the SARS-CoV-2 virus is 180-200 kDa, in size, and is 1273 amino acids long. It consists of an extracellular domain, a transmembrane domain, which is buried in the viral membrane, followed by a cytoplasmic domain, which is totally inside of the viral membrane (3). At the N-terminal end of the S protein, which starts outside of the viral membrane in the "extracellular domain", is a signal peptide which is just 13 amino acids long (3).

The S1 subunit is next and is composed of amino acids 14-685 (3). The S1 subunit contains the N-terminal domain (amino acids 14-305) followed by a receptor-binding domain (RBD) extending from amino acids 319-541 (the receptor involved is the ACE2 receptor of the human cells (2, 3, 5, and 6). The function of the S1 subunit is attachment of the virus to the plasma membrane of cells through binding of the RBD of the virus to the ACE2 receptor which is expressed on most human cells (2, 3, 5, and 6). This first step in the infection of human cells by the SARS-CoV-2 virus.

The S2 subunit of the Spike Protein extends from amino acid residue 686 to amino acid residue 1273 which plays a role in the fusion of the viral membrane to the plasma membrane which results in the internalization of the virus within the plasma membrane of the cell (3). The S2 subunit has the following domains: the fusion peptide (FP) which extends from amino acid residue 788 to amino acid 806), the heptapeptide repeat sequence 1 (HR1), which extends from amino acid 912 to amino acid residue 984, the heptapeptide repeat sequence 2 (HR2) which extends from amino acid 1163 to amino acid 1213, the transmembrane (TM) domain (extending from amino acid 1213 to amino acid 1237), and the last domain which is the cytoplasmic domain (CD) which extends from 1237 to amino acid 1273 (3).

The viral Spike Protein (S) assembles itself into homotrimers (5) composed of a "bulbous" head (S1) resting on a stalk (S2). Binding of the viral RBD to the cellular ACE2 receptor activates cellular proteases which cleave the viral S protein into two subunits, S1 and S2. This produces a change in the conformation of the viral Fusion Protein (FP) which causes it to fold and enter into the plasma membrane of the host cell (3). The entry of the FP into the plasma membrane of the host cell disrupts the stability of the lipids in the cellular plasma membrane resulting ultimately in the fusion of the viral membrane and the plasmid lipid membrane of the human cell (2, 3).

Applicant's Prior Work

The original MicroVAX vaccine was an Ad-sig-TAA/ecdCD40L adenoviral vector DNA vaccine, where the sig is an intracellular secretory trafficking signal, and the TAA is the target associated antigen (TAA) on the cancer cell or infectious agent. This vaccine was designed to promote the uptake of the TAA/ecdCD40L fusion protein by dendritic cells by binding to the CD40 receptors on the antigen presenting or dendritic cells), that then present the TAA fragments on the Class I and Class II MHC complexes on the surface of the dendritic cell.

Applicant has gained extensive experience in experimenting with fusion proteins and has gained a good understanding of their biological activity, and realized that in addition to an adenoviral approach, a mRNA vaccine approach might additionally be employed for the SARS-CoV-2 virus epidemic outbreak in connection with a fusion protein application for a COVID-19 vaccine. For examples of the structure and operation of the original TAA/ecdCD40L MicroVAX vaccine see one or more of the following U.S. Pat. Nos. 8,119,117; 8,299,229; 8,828,957; and 9,533,036 which are hereby incorporated herein by reference.

Description of the TAA/ecdCD40L Composition/Vaccine Platform. All vaccines and compositions defining a vaccine have the same basic goal: to increase the level of cells in the body that can recognize a specific antigenic structure and generate an antibody and/or a CD8 effector T cell lymphocyte immuno-stimulatory response against cells bearing the targeted antigenic structure. The antigenic structure is usually associated with a specific threat or an infectious agent. Conventional vaccines may consist of the injection, under the skin (sc) or into a muscle (im), a weakened or inactivated version of a virus or cancer cell or some "recognizable" part of a protein or carbohydrate structure derived from a cancer cell or from a virus. This antigenic target will be referred to as a Target Associated Antigen (TAA).

The TAA/ecdCD40L fusion vaccine composition can also be incorporated into a RNA translation unit so that it can be converted into protein once the RNA vector is injected, for example, into muscle. RNA expression vectors are often wrapped up in tiny lipid droplets called lipid nano-particles (LNPs) or lipid micro-particles (LMPs) to protect the RNA from being destroyed.

RNA vaccines/compositions have been shown to have advantages over DNA viral vaccines with respect to the ease, rapidity and lower cost with which the manufacturing process can be carried out. But the RNA vaccines need to be stored as a frozen solution to make the product stable for storage for long periods of time. However, it is believed that RNA vaccines may initially induce a greater immune response in magnitude than do the viral expression vectors. On the other hand, the level of the immune response may persist for a shorter period of time in RNA expression vectors. Therefore, there may be a need with RNA immunization for additional injections for "boosting" or re-induction of the immune response with additional vaccinations and that will persist for longer periods of time. In contrast, Applicant is of the belief that the preferred vaccine composition embodiment described in the detailed prophetic example articulated below, will provide protection that will persist for at least one year.

ABBREVIATIONS

Figure 1:
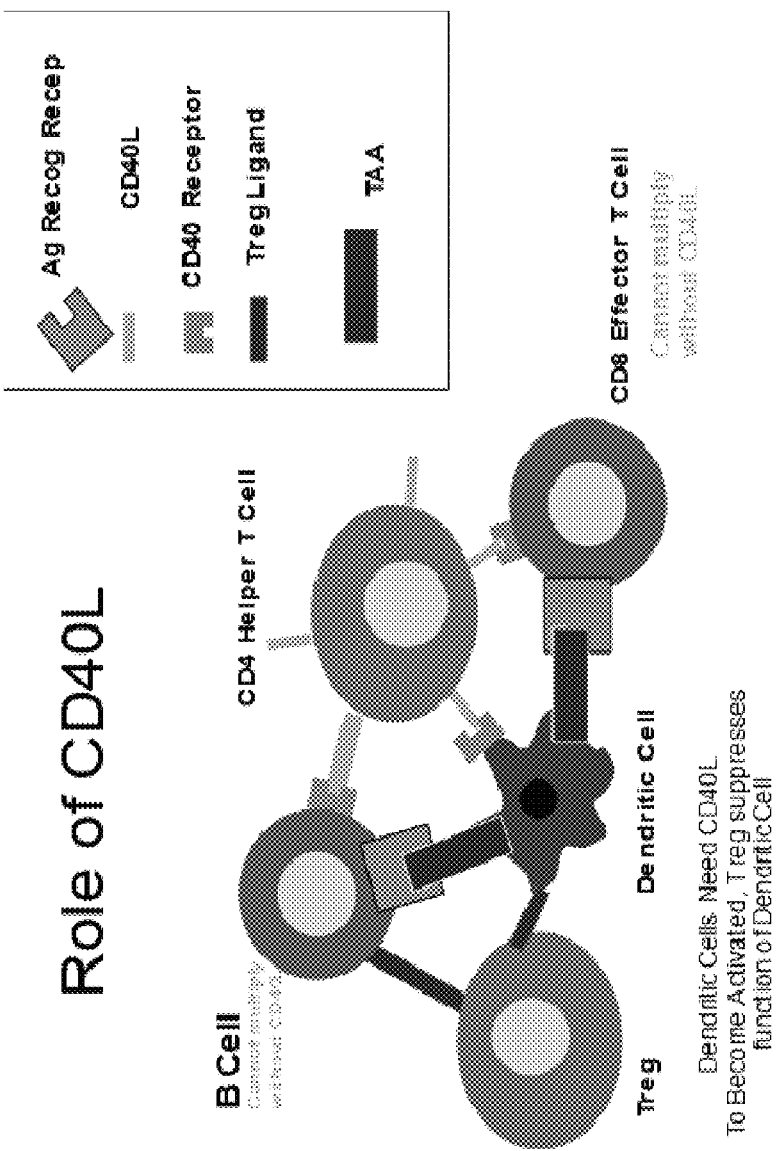
FIG. 1 shows the attachment of the TAA to the CD40L accomplishes two things: (i) the binding of the TAA/ecdCD40L protein to the CD40 receptor on dendritic cells (DC) as well as one the B cells and T cells, activating these cells thereby promoting a potent immune response, and (ii) once the TAA/ecdCD40L protein is engaged on the CD40 receptor on the DC, the entire TAA/ecdCD40 L protein is internalized into the DC in a way that allows Class I as well as Class II MHC presentation of the TAA.

TMD: The TMD or transmembrane domain of the non-secretable sig-TAA-TMD/ecdCD40L fusion protein could be a segment comprising the entire TMD or a significant portion thereof (in a preferred embodiment), the CD40L transmembrane domain being about 24 amino acids in length. Alternatively, the TMD could be the transmembrane domain of the Targeted Associated Antigen (if present), assuming this is suitable for a particular situation at hand. The transmembrane domain of human CD40L is 23 AA, where the transmembrane domain is in positions 23-46 of CD40L which is 261 AA in length. See U.S. Pat. No. 8,119,117 in which Applicant is a co-inventor, which patent is hereby incorporated herein by reference.

TAA: Target Associated Antigen, associated with the infectious agent of interest (antigen specific)
   sig: secretory sequence
     CD40L: CD40 ligand which is an immunostimulatory protein ecd: extracellular domain could be the entire extracellular domain of human CD40L or a significant segment thereof or the extracellular domain of another human costimulatory molecule.
   UTR: untranslated region
   CAP: 5' end of RNA molecule
   Poly AAAAA Tail: 3' end of RNA molecule
   LMP: lipid microparticle: RNA vaccine wrapped in lipid microparticles.
   APCs: Antigen Presenting Cells
   TL/TLU: Translation unit—a basic unit of compilation or a single source file
   (im) or IM: intramuscular
   mRNA: messenger RNA
   LNP: lipid nanoparticles
   SFSP: Selected Fragment of the Spike Protein
   Dosing Amounts: Reasonable or effective amounts of dosing level treatments for the infectious disease areas relating to fusion proteins (TAA/ecdCD40L and TAA-TMD/ecdCD40L), are disclosed in U.S. Pat. Nos. 8,119,117; 8,299,229 and 9,533,036, in each of which the current inventor is a co-inventor, and which patents are hereby incorporated herein by reference.

DETAILED DESCRIPTION

SARS-CoV-2 Fusion Protein General Strategy

Applicant's strategy is initially designed around utilizing the previously designed TAA/ecdCD40L composition/vaccine platform (9-19), but with seven uniquely selected peptides from the Spike Protein of the SARS-CoV-2 which are encoded in adenoviral expression vector or encoded in the translation unit of a mRNA vaccine encapsulated in liposome nano particles (LNP). In bringing an immunotherapeutic vaccine for the public's benefit, many of the companies used this new vaccine delivery technology call messenger RNA or mRNA, as opposed to older vaccine DNA technology, which new technology has certain advantages in terms of expense of manufacture and in advancing the speed at which a commercial vaccine manufactured in large quantities can be brought to meet the public's need.

A SARS-CoV-2 Fusion Protein for mRNA vaccine in which the mRNA encoding the extracellular domain (ecd) of the CD40L co-stimulatory molecule (9-19), is attached individually to mRNA encoding a multiple of distinct peptide fragments, preferably 7 fragments, each preferably selected from a different region of the Spike Protein (S) of the SARS-Cov-2 virus. The binding of the S protein to the angiotensin converting enzyme-2 (ACE2) receptor protein on human cells enables the SARs-CoV-2 virus to attach to and then infect human cells. A mixture composition of multiple mRNA vectors, designed for injection, preferably intramuscularly, and each fragment joined to the extracellular domain (ecd) of the CD40L, are described as a regimen or vaccine strategy for SARS-CoV-2 virus that has the capability to suppress the emergence of immunological escape mutants. Each fragment is designed to activate a humoral and cellular immune response.

This vaccine strategy is designed to activate both a humoral and cellular immune response to each of seven different fragments of the SARS-CoV-2 virus including fragments of the subunit S1 (amino acids 14-685) and subunit S2 (amino acids 686-1273), of the Spike Protein (S1 and S2 respectively) preferably comprising a single mixed composition of seven different encoded S protein fragments to minimize the probability of variant viruses arising through mutational change in the Spike Protein.

Each of the seven target associated antigens (TAAs) are chosen from different regions of the Spike Protein (S). Each one is fused to the extracellular domain (ecd) of the immuno-stimulatory protein CD40 ligand (ecdCD40L), thereby forming 7 distinct TAA/ecdCD40L chimeric proteins, wherein preferably three (SEQ ID NOS 1-3) of said TAA are from subunit #1 (S1) of the Spike Protein and preferably four (SEQ ID NOS 4-7) of said TAA are from subunit #2 (S2) of the Spike Protein (S), and wherein each TAA contains amino acid domains or domain regions which bind to and are recognized by Class I MHC and Class II MHC for inducing neutralizing antibodies and activating dendritic cells, B cells and T cells. Each of the seven separate fragments are stabilized by collectively taking advantage of the combined effect of both the homotrimeric characteristics of the Spike Protein functional regions and the homotrimeric characteristics of the immuno-stimulatory CD40L protein.

The binding of the S protein to the angiotensin converting enzyme-2 (ACE2) receptor protein on human cells enables the SARS-CoV-2 virus to attach to and then infect human cells. A preferred mixture composition of different mRNA molecules each containing a different SFSP/ecdCD40L fusion protein translation unit or a single strand of mRNA containing 7 different SFSP/ecdCD40L translation units in a linear array, and each SFSP fragment joined to the extra-cellular domain (ecd) of the CD40L are described as a vaccine strategy for SARS-CoV-2 virus that has the capability to suppress the emergence of immunological escape mutants.

The fact that this composition/vaccine is multivalent, a multiple of antigenic targets and preferably the 7 different antigenic targets disclosed below from the SARS-CoV-2 Spike protein), and that many of the fragments are from regions which are functionally distinct, and that each target associated antigen is linked to an ecdCD40L immunostimulatory protein and therefore induces a potent immune response, is the basis that makes this regimen or vaccine able to suppress the emergence of immunological escape mutants.

mRNA TAA/ecdCD40L Vaccine

We are proposing a SARS-CoV-2 mRNA regimen or vaccine in which a mRNA encoding the extra-cellular domain (ecd) of the immuno-stimulatory protein, CD40 ligand (ecdCD40L), will be attached individually to mRNA encoding each of 7 peptides selected from the Spike Protein (S) of the SARS-Cov-2 virus in a translation unit of the mRNA vaccine. This is referred to as the MicroVAX TAA/ecdCD40L Composition/Vaccine for SARS-CoV-2 where TAA stands for "Target Associated Antigens". In this composition/vaccine, the TAA are the fragments of the S protein which are attached to the ecdCD40L (see below) in the section entitled: "Prophetic Example—Structure of mRNA Vaccine Carrying a Transcription Unit Encoding a TAA/ecdCD40L Vaccine" where the TAA are composed of 7 different fragments of the Spike Protein of the SARS-CoV-2 Virus. The stability of the TAA/ecdCD40L composition/vaccine fusion protein is increased by the fact that both the Spike Protein fragments and the ecdCD40L both contain amino acid sequences that spontaneously form homotrimers in solution.

The design is intended to induce increased levels of antibodies or CD8 effector T cell lymphocytes specific for each of the TAA or SFSP (fragments of the Spike Protein of the SARS-CoV-2 which are attached to an ecdCD40L) are monitored with ELISA and ELISPOT assays respectively. The methods for these assays for anti-TAA antibodies and for TAA specific CD8 effector T cells are outlined in references 1-8 and 13. The fact that this composition/vaccine is multivalent (7 different antigenic targets on the Spike protein), and that each target associated antigen is linked to an ecdCD40L immunostimulatory protein, is the basis that makes this composition/vaccine able to suppress the emergence of immunological escape mutants.

Vaccination is carried out preferably by injecting intramuscularly a composition which includes a mixture of the 7 TAA/ecdCD40L mRNA vaccines described below, or alternatively a single mRNA strand which contains 7 different SFSP/ecdCD40L translation units in linear array.

Description of the TAA/ecdCD40L Composition/Vaccine Platform

All vaccines and compositions defining a vaccine have the same basic goal: to increase the level of cells in the body that can recognize a specific antigenic structure and generate an antibody and/or a CD8 effector T cell lymphocyte immuno-stimulatory response against cells bearing the targeted antigenic structure. The antigenic structure is usually associated with a specific threat (a cancer cell or an infectious agent). Conventional vaccines may consist of the injection, under the skin (sc) or into a muscle (im), a weakened or inactivated version of a virus or cancer cell or some "recognizable" part of a protein or carbohydrate structure derived from a cancer cell or from a virus. This antigenic target will be referred to as a Target Associated Antigen (TAA).

The goal of these injections is to provide the immune response the opportunity to become familiar with the target associated antigen in a setting in which there is no threat of disease so that the body can learn how to detect and suppress the antigen bearing cancer cell or virus. The vaccination/administration can be as simple as injection of an inactivated infectious agent or cancer cell. An adjuvant or antigenic enhancer is usually added to the antigenic target. The antigenic structure used for the vaccination can be encoded in the transcription unit of a DNA expression vector, mRNA vector or of a plasmid expression vector.

The original composition/vaccine was based on the attachment of a fragment of a target associated antigen (TAA) fused to the extracellular domain (ecd) of the potent immunostimulatory signal CD40 ligand (CD40L). The composition/vaccine was an adenoviral expression vector which was administered as a single subcutaneous injection on a given day for adenoviral expression vectors encoding the TAA/ecdCD40L.

This TAA/ecdCD40L composition/vaccine platform was developed by the Applicant's laboratory (9-19) to overcome the following problems: weak immunogenicity of the target antigens, qualitative or quantitative defects of CD4 helper T cells, defective response in immunodeficient individuals including the older aged population due to diminished expression of CD40L in activated CD4 helper T cells, and/or low levels of presentation of target antigens on Class I or II MHC in dendritic cells (DCs). As shown in FIG. 1, the CD40L is important for the expansion of antigen specific CD8 effector T cells and antigen specific B cells, as well as memory B and T cells, in response to vaccination.

The TAA is connected through a linker to the aminoterminal end of an ecd of the potent immunostimulatory signal CD40L. The attachment of fragments of the TAA to the CD40L accomplishes two things as shown in FIG. 1: (i) the binding of the TAA/ecdCD40L protein to the CD40 receptor on the DCs as well as on the B cells and T cells, activating these cells thereby promoting a potent immune response (14, 16, 18), and (ii) once the TAA/ecdCD40L protein is engaged on the CD40 receptor of the dendritic cell (DC), the entire TAA/ecdCD40L protein is internalized into the DC in a way that allows Class I as well as Class II MHC presentation of the TAA (14, 18).

Figure 2:
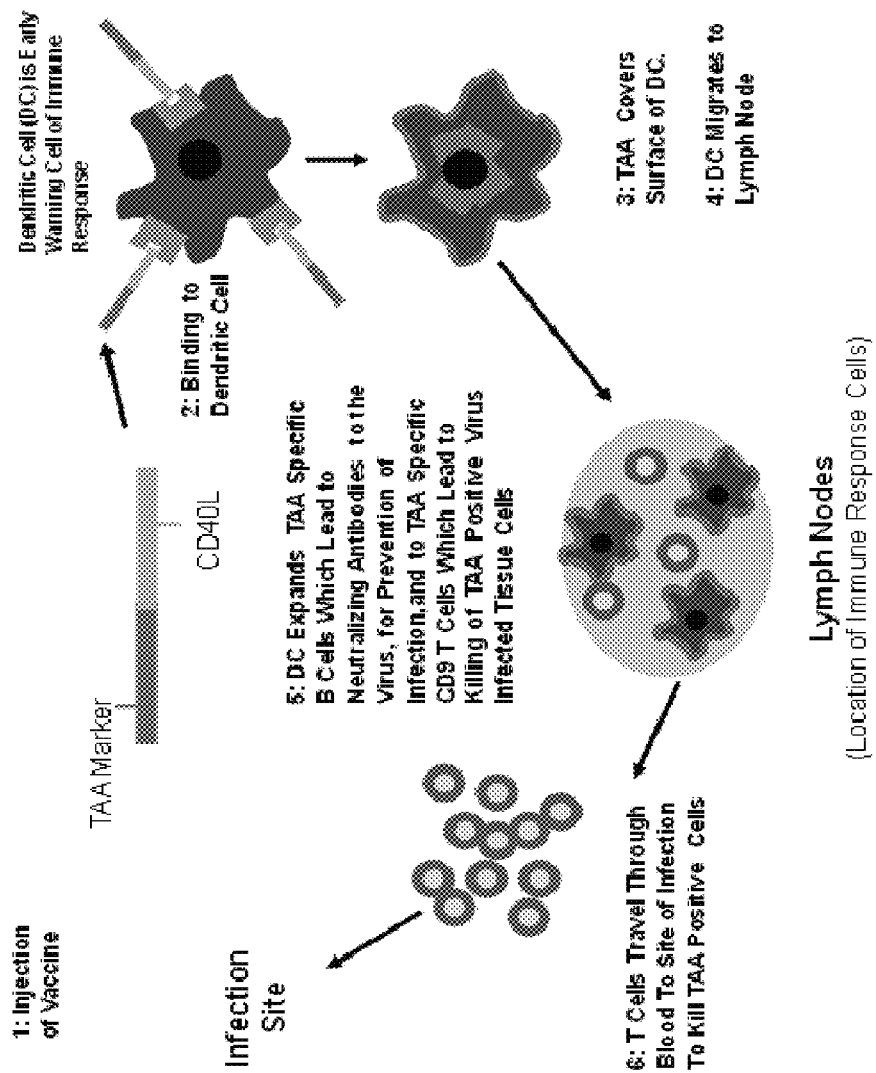
FIG. 2 shows the induction of the adaptive immune response with the TAA/ecdCD40L vaccine. The CD40L end binds to the CD40 receptor on DCs leading to the internalization of the TAA.

The activated TAA loaded DCs then migrate to the regional lymph nodes (9, 11, 13) where they can activate and induce expansion of the TAA specific CD8+ effector T cells. As shown in FIG. 2, these antigen specific CD8+ effector cells become increased in number in the lymph nodes (9, 11, 13), and they then egress from the lymph nodes into the peripheral blood. The antigen specific CD8 effector T cells exit the intravascular compartment and enter into the extravascular sites of inflammation or infection (19). In addition to showing that this vaccine increases the levels of the antigen specific CD8+ effector T cells in the sites of inflammation or infection (19), the Applicant's laboratory has shown that the activation and expansion of the B cells by the TAA/ecdCD40L protein increases the levels of the TAA specific antibodies (including neutralizing antibodies against viral antigens) in the serum (9-19).

Prophetic Example—Structure of a mRNA Vaccine Carrying a Transcription Unit Encoding a TAA/ecdCD40L Vaccine The structure of each of the 7 TAA/ecdCD40L fusion proteins is shown below. In each case, the amino acid residue numbers of the Spike Protein fragments as presented in reference 3, is used to characterize the composition of the TAA or fragment of the Spike Protein used.

1. Psig-RBD$_{327-380}$/ecdCD40L, where sig is the 13 amino acid residue signal peptide linked to amino acid 327 of the Receptor Binding Domain (RBD) of S1 of SARS-CoV-2, RBD$_{327-380}$ is the first half region of the Receptor Binding Domain of S1 of SARS-CoV-2 (AA327-380), which is linked to ecdCD40L which is the extracellular domain of the CD40 ligand.

Seq. ID No. 1 (The AA sequence of AA 327-380): VRFPNITNLCPFGEVFNATRFASVYAWNRKRIS-NGVADYSVLYNSASFSTFKCY. (From: Walls A G et al. Structure, function and antigenicity of the SARS-CoV-2 Spike. Cell 180:281-292, 2020.)

2. Psig-RBD$_{381-441}$/ecdCD40L, where sig is the 13 amino acid residue signal peptide linked to amino acid 381 of the Receptor Binding Domain (RBD) of S1 of SARS-CoV-2, RBD$_{381-441}$ is the second half region of the Receptor Binding Domain of S1 of SARS-CoV-2 (AA381-441), which is linked to ecdCD40L which is the extracellular domain of the CD40 ligand.

The Seq. ID No. 2 (The AA sequence of AA 381-441): GVSRTKLNCLCFTNVYADSFVIR-GDEVRQIAPGQTCKIADYNYKLPDDFTGCVI-AWNSN NL. (From Walls A G et al Cell 180: 281-292, 2020.)

3. Psig-FP$_{788-806}$/ecdCD40L, where sig is the 13 amino acid residue signal peptide linked to amino acid 788 of the Fusion Protein (Fp) of S1 of SARS-CoV-2, FP$_{788-806}$ is the Fusion Protein Domain of S2 of SARS-CoV-2 (AA788-806), which is linked to ecdCD40L which is the extracellular domain of the CD40 ligand.

The Seq. ID No. 3 (The AA sequence of 812-855): SFIEDLLFNKVTLADAGFIKQYGDCLGDI-AARDLICAQKR. (From Antiviral Research 178: 2020; 104792 NCBI Genbank SARS-CoV-2 (MN 908947.3)

4. Psig-HRS1$_{912-948}$/ecdCD40L, where sig is the 13 amino acid residue signal peptide linked to amino acid 912 of the Heptapeptide Repeat Sequence 1 (HRS1) of S1 of SARS-CoV-2, HRS1$_{912-948}$ is the Heptapeptide Repeat Sequence 1 Domain of S2 of SARS-CoV-2 (AA912-948), which is linked to ecdCD40L which is the extracellular domain of the CD40 ligand.

The Seq. ID No. 4 (The AA sequence of 812-855): SFIEDLLFNKVTLADAGFIKQYGDCLGDI-AARDLICAQKR. (From: Antiviral Research 178: 2020; 104792 NCBI Genbank SARS-CoV-2 (MN 908947.3))

5. Psig-HRS2$_{1163-1213}$/ecdCD40L, where sig is the 13 amino acid residue signal peptide linked to amino acid 1163 of the Heptapeptide Repeat Sequence 2 Domain of S2 of SARS-CoV-2, HRS2$_{1163-1213}$ is the Heptapeptide Repeat Sequence 2 of S2 of SARS-CoV-2 (AA1163-1213), which is linked to ecdCD40L which is the extracellular domain of the CD40 ligand.

The Seq. ID No. 5 (The AA sequence of 1163-1213): DISGINASVVNIQKEIDRLNESLIDLQEL. (From Xia S et al Cell Mol Immunology 17: 765, 2020)

6. Psig-TM$_{1205-1242}$/ecdCD40L, where sig is the 13 amino acid residue signal peptide linked to amino acid 1205 of the Transmembrane Domain (TD) of S2 of SARS-CoV-2, TM$_{1205-1242}$ is the Transmembrane Domaine of S2 of SARS-CoV-2 (AA1205-1242), which is linked to ecdCD40L which is the extracellular domain of the CD40 ligand.

The Seq. ID No. 6 (The AA Sequence of 1205-1242): LGFIAGLI-AIVMVTIMLCCMTSCCSCLKGCCSCGSCC. (From Xia X H. Domains and Functions of Spike Protein in SARS-CoV-2 in the context i=of Vaccine Design. Viruses 13: 109, 2020.)

7. Psig-CD$_{1237-1273}$/ecdCD40L, where sig is the 13 amino acid residue signal peptide linked to amino acid 1237 of the Cytoplasmic Domain (CD) of S2 of SARS-CoV-2, CD$_{1237-1273}$ is the Cytoplasmic Domain of S2 of SARS-CoV-2 (AA1237-1273), which is linked toecDC40L which is the extracellular domain of thCD40 ligand The Seq. ID No. 7 (The AA Sequence of 1234-1273): LCCMTSCCSCLKGCCSCGSCCKFDEDD-SEPVLKGVKLHYT. (From: Buonvino S and Melino Sonia. New Consensus pattern in Spike CoV-2 potential implications in Coagulation process and cell-cell fusion. Cell Death Discovery, 6: 134-138, 2020.)

Therapeutic Goals for a SARS-CoV-2 Composition/Vaccine
Major therapeutic goals for a critically needed successful SARS-CoV-2 composition or vaccine, not heretofore developed, include:

1. Preventing the infection of human cells by the SARS-CoV-2 virus and its subsequent replication within these cells by inducing high titers of antibodies to the TAA polypeptides derived from the S protein. This accomplished by inhibiting the binding and uptake of SARS-CoV-2 into human cells which is necessary for the replication of SARS-CoV-2.

2. A reduction in the infectivity of the SARS-CoV-2 by the binding of neutralizing antibodies to the Spike Protein (S) involved in the binding to the ACE2 receptor on human cells and subsequent uptake of SARS-CoV-2 virus. The binding of the RBD of the S protein induces the conversion of the S protein into the S1 and S2 protein subunits which contain the fragments outlined in in the preceding section. These fragments are converted into potent immunogens by linking them to the ecdCD40L.

3. Protecting vaccinated individuals from SARS-CoV-2 infection at least during the first year following the vaccination. Previous experiments with the TAA/ecdCD40L platform have shown (see references 11 and 13) that the memory response to the TAA/ecdCD40L vaccine lasts at least a year. In reference (24), the memory response has been following an infection with SARS-CoV-2 for 8 months.
4. Suppressing the evolution of mutant variant strains of SARS-CoV-2 by inducing antibodies to 7 antigenic sites on the SARS-CoV-2 S protein simultaneously, each of which are attached to the ecdCD40L.
5. The TAA/ecdCD40L results in binding of TAA fragments to both Class I and Class II MHC recognition, thereby generating a protective cellular as well as humoral immune response.

In addition, specific strategies outlined above and below are novel and previously not conceived of in a previously reported vaccine strategy for SARS-CoV-2, in that previously reported vaccines for SARS-CoV-2 virus have not proposed to induce antibodies with compositions/vaccines using the TAA/ecdCD40L platform.

Increasing the immunogenicity of a plasmid DNA vaccine through linking the S protein TAA fragments to the ecdCD40L immunostimulatory protein promotes a potent adaptive immune response.

Applicant has elected to employ Applicant's TAA/ecdCD40L vaccine platform in the following manner as a preferred embodiment, defining criteria for a SARS-CoV-2 vaccine and which meets the above identified goals:
1. The IM administration of a single mixture of mRNA encoding TAA/ecdCD40L protein vaccines in which the TAA derived from the S protein will induce very-high titer levels of antibodies to these S peptide fragments proteins resulting in a reduction of infectivity of the S protein of the SARS-CoV-2 and will prevent the entry of the SARS-CoV-2 into the human cells which it must enter to replicate.
2. The attachment of the S derived TAA listed in section on the structure of the Spike Protein (see pp 5-6) to the aminoterminal end of the ecdCD40L, to convert these immunogens into potent immunogens and thereby induce very-high titer levels of neutralizing antibodies to these peptides such that the SARS-C-2 organism no longer binds to the ACE2 receptor on human cells nor is taken up by these cells.
3. The collective administration of 7 mRNA vaccines which encode TAA derived from the S protein fragments attached to the aminoterminal end of the ecdCD40L induce levels of anti-S antibodies that are completely protective (through a humoral as well as cellular immune response) of vaccinated individuals against infection by the SARS-CoV-2 virus.
4. The collective administration of mRNA vaccines which encode the S protein fragments listed above in the section on the structure of the "Spike Protein" attached to the aminoterminal end of the ecdCD40L to induce memory cells such that the protection against SARS-CoV-23 will last greater than one year.

Strategy for Prevention of Mutant Variant Forms of SARS-CoV-2 which have Increasing Resistance to Neutralizing Antibodies Induced by Existing Vaccines for the SARS-CoV-2 Virus The imposition of a negative selective pressure against a single target antigen in a virus which is genetically unstable and has a high transmissibility rate, is that the viral population will shift such that a new form of the virus appears which can escape from the antigen which mediates the negative selection. To counter this immunological escape from occurring, Applicant generates a mixture of TAA/ecdCD40L vaccines preferably against 7 independently derived target associated antigens (TAA) each generally derived from a functionally distinct and independent regions of the S protein. Each of these 7 vaccines will be directed to a different antigen which plays a critical important and functionally distinct role in the infectious process ($TAA_{n=1-10}$/ecdCD40L). Each of these 7 vaccines can induce neutralizing antibodies again separate and distinct regions of the S protein. In order for a variant strain to arise to a position of dominance in the population, it would have to have 7 new mutations, allowing it to simultaneously escape each of 7 TAA. The probability of this happening is extremely low.

Creating a Mixture of mRNA Fragments Encapsulated in LMP or LNP which Encode Chimeric Proteins Composed of a Different Spike Protein Fragment Attached to the Immunostimulatory ecdCD40L:

As outlined below, the vaccine strategy is to create a mixture of mRNA molecules each encapsulated in LMP which encode 7 vaccines each one encoding a TAA/ecdCD40L vaccine fusion protein in which the TAA was taken from different domain regions (three regions) of the Spike Protein S1 subunit and a different domain (four domains) of the Spike Protein S2 subunit, each of which four domain is functionally distinct. Both the S protein fragments and the ecd of the CD40 ligand form homotrimers. Since this increases the length of the polypeptide backbone that is involved in the homotrimeric array, the stability of the TAA/ecdCD40L homotrimer will increase.

Unique Advantages of the Applicant's Composition/Vaccine:

The advantage of the TAA/ecdCD40L platform is that this 7 mRNA vaccine mixture will for different target associated antigens be more potent as vaccines than other methods of vaccination. This has been shown for several different antigens related to both cancers and infectious diseases (9-19).

The unique vaccine platform induces high titers of neutralizing antibodies even against weakly immunogenic Target Associated Antigens (TAA), as well as efficient presentation by dendritic cells (DC) to T cells and B cells (9-19). In the TAA/ecdCD40L vaccine, the TAA is connected to the amino-terminus of the extracellular domain (ecd) of the potent immuno-stimulatory signal CD40 ligand (CD40L).

The attachment of each of the TAA to an ecdCD40L accomplishes: (i) Activation of DCs as well as B cells and T cells via the binding of the TAA/ecdCD40L protein to the CD40 receptor on these cells (11), and (ii) Class I MHC & Class II MHC antigen presentation.

TAA/ecdCD40L protein binding to the CD40 receptor of the DC, and internalization into the DC (11). The TAA/ecdCD40L composition/vaccine increases the levels of the TAA specific antibodies in the serum as well as the levels of TAA specific CD8 effector T cells in the sites of tissue inflammation (11, 13). The TAA/ecdCD40L vaccine induces memory for over a year (9, 11) and converts weak immunogens (TAA) into strong or potent immunogens in younger as well as in older test subjects (16). The TAA/ecdCD40L vaccine induces titers of neutralizing antibodies of up to 1/4000 for some viral antigens (16). The TAA/ecdCD40L vaccine platform has already reached clinical trials in human subjects for cancer vaccine application (19).

Figure 3:
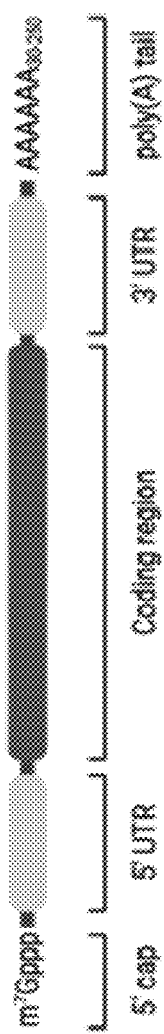
FIG. 3 is a representation of the conventional structural elements of a mRNA vaccine depicting a coding region containing a disease antigen to be targeted, in which the secretable fusion protein composition may be employed.

In application of an appropriate mechanism this second part of Applicant's strategy, with regard to the muti-fragmented mixture composition, one might use a messenger RNA (mRNA) which has the following standard components as shown in FIG. 3, for an mRNA composition/vaccine: 5' CAP-5' UTR-Translation Unit which has a strand of RNA encoding a standard sig-TAA/ecdCD40L secretable fusion protein composition/vaccine.

Antigen-presenting cells (APCs) are a heterogeneous group of immune cells that mediate the cellular immune response by processing and presenting antigens for recognition by certain lymphocytes such as B and T cells lymphocyte cells. Classical APCs include dendritic cells, macrophages, Langerhans cells and B cells. Dendritic cells are considered to have the broadest range of antigen presentation and are necessary for activation of naive T cells. DCs present antigen to both helper and cytotoxic T cells. They can also perform cross-presentation, a process by which they present exogenous antigen on MHC class I molecules to cytotoxic T cells. In the myofibers (muscle fibers), facultative antigen presenting cells myoblasts, myocytes and myotubes which express the CD40 receptor to engage the sig-TAA/ecdCD40L fusion protein to generate a humoral as well as cellular immune response.

The inventive mRNA vaccine described above and/or dual encoding technique, may be administered intra-muscularly, intra-dermally, orally and/or subcutaneously, although intra-muscularly is preferred.

Sequence Listing:
- Seq. ID No. 1 (The AA sequence of AA 327-380): VRFPNITNLCPFGEVFNATRFASVYAWNRKRIS-NGVADYSVLYNSASFSTFKCY
- Seq. ID No. 2 (The AA sequence of AA 381-441): GVSRTKLNCLCFTNVYADSFVIR-GDEVRQIAPGQTCKIADYNYKLPDDFTGCVI-AWNSN NL. (From Walls A G et al Cell 180: 281-292, 2020.)
- Seq. ID No. 3 (The AA sequence of 812-855): SFIEDLL-FNKVTLADAGFIKQYGDCLGDIAARDLICAQKR. (From Antiviral Research 178: 2020; 104792 NCBI Genbank SARS-CoV-2 (MN 908947.3)
- Seq. ID No. 4 (The AA sequence of 812-855): SFIEDLL-FNKVTLADAGFIKQYGDCLGDIAARDLICAQKR. (From: Antiviral Research 178: 2020; 104792 NCBI Genbank SARS-CoV-2 (MN 908947.3))
- Seq. ID No. 5 (The AA sequence of 1163-1213): DISGI-NASVVNIQKEIDRLNESLIDLQEL. (From Xia S et al Cell Mol Immunology 17: 765, 2020)
- Seq. ID No. 6 (The AA Sequence of 1205-1242): LGFIA-GLIAIVMVTIMLCCMTSCCSCLKGCCSCGSCC. (From Xia X H. Domains and Functions of Spike Protein in SARS-CoV-2 in the context i=of Vaccine Design. Viruses 13: 109, 2020.)
- Seq. ID No. 7 (The AA Sequence of 1234-1273): LCCMTSCCSCLKGCCSCGSCCKFDEDD-SEPVLKGVKLHYT. (From: Buonvino S and Melino Sonia. New Consensus pattern in Spike CoV-2 potential implications in Coagulation process and cell-cell fusion. Cell Death Discovery, 6: 134-138, 2020.)

REFERENCES

1. Wrapp D, Wang N, Corbett K S, Goldsmith J A, Hsieh C L, Abiona O, Graham B S and McLellan J S. Cryo-EM structure of the 2019-hCoV spike in the prefusion conformation. Science 367: 1260-63, 2020.
2. Lan J, Ge, J W. Yu J F, Shan S S, Zhou H, Fan S L, Zhang Q, Shi, X T, Wang Q H, Zhang lQL, and Wang X Q. Structure of the SARS-CoV-2 spike receptor binding domain bound to the ACE2 receptor. Nature 581: 215-220, 2020.
3. Huang Y, Yang C, Xu X F, Xu W, and Liu S W. Structural and functional properties of SARS-CoV-2 spike protein: Potential antivirus drug development for COVID-19. Acta Pharmacological Sinica. 41:1141-1149, 2020.
4. Wang C, Wentao L, Dubravka D, Nisreen O, van Haperen R, Osterhaus A, van Kuppeveld F, Haagmans B L, Grosveld F, and Bosch B J. A human monoclonal antibody blocking SARS-CoV-2 Infection. BioRxiv Preprint domain
5. Wang Q H, Zhang Y F, Wu L L, Zou H, Yan J H, and Qi J X. Structural and functional basis of SARS-CoV-2 entry by using human ACE2. Cell 181, 894-904, 2020.
6. Walls A C, Park Y J, Tortorici M A, Wall A, McGuire A T, and Veesler D. Structure, function and antigenicity of the SARS-CoV-2 Spike glycoprotein. Cell 180: 281-292, 2020
7. Hou Y J, Chiba S H, Halfmann P, Ehre C, Kuroda M, Lee R E, Mascenik T M, Graham R, Edwards C E, Tse L V, Okuda K, Markmann A J, Bartelt L, de Silva A, Margolas D M, Boucher R C, Randell S H, Suzuki T, Gralinski L E, Kawaoka Y, and Baric R S. SARS-CoV-2 D614Gg variant exhibits efficient replication ex vivo and transmission in vivo. Science 10.1126/science.abe8499 (2020).
8. Lasek-Nesselquist E, Lapierre P, Schneider E, St. George, and Pata J, The locadlized rise of a B.1.526nSARS-CoV-2 variant containing an E484K mutation in NewYork State.
9. Zhang, L, Tang, Y, Akbulut H, Zelterman D, Linton P-J, and Deisseroth, A. An adenoviral vector cancer vaccine that delivers a tumor-associated antigen/CD40-ligand fusion protein to dendritic cells. PNAS, 100: 15101-15106, (2003).
10. Akbulut, H, Tang, Y, Maynard J, Zhang L, Pizzorno G, and Deisseroth, A. Vector targeting makes 5-fluorouracil chemotherapy less toxic and more effective in animal models of epithelial neoplasms. Clin Cancer Res 10: 7738-7746, (2004).
11. Tang, Y, Zhang, L, Yuan, J, Akbulut H, Maynard J, Linton P-J, and Deisseroth, A. Multistep process through which adenoviral vector vaccine overcomes anergy to tumor-associated antigens. Blood, 104: 2704-2713, (2004).
12. Akbulut H, Tang Y C, Akbulut K G, Maynard J, Zhang L, Deisseroth A. Antitumor immune response induced by i.t. injection of vector activated dendritic cells and chemotherapy suppresses metastatic breast cancer. Mol Cancer Ther 5:1975-1985, (2006).
13. Tang Y C, Maynard J, Akbulut H, Fang X M, Zhang W W, Xia X Q, Koziol J, Linton P-J, and Deisseroth A. Vaccine which overcomes defects acquired during aging and cancer. Journal of Immunology 177:5697-5707, (2006).
14. Tang Y, Akbulut H, Maynard J, Zhang L, Petersen L, and Deisseroth A. Vaccine strategies for cancer and infectious diseases in the elderly. Gene Therapy, Eds. Takenori Ochiai, Hideaki Shimada, and Masatoshi Tagawa, Published by Japanese Ministry of Education and Science, pp. 78-85, (2007).
15. Akbulut H, Akbulut K G, Tang Y C, Maynard J and Deisseroth A. Chemotherapy targeted to cancer tissue potentiates antigen specific immune response induced by vaccine for In vivo antigen loading and activation of dendritic cells. Molecular Therapy, 10:1753-1760, (2008).
16. Tang, Y C, Linton, P J, Thoman M, and Deisseroth A. Symposium in Writing: Vaccine for infections and cancer. Cancer Immunology and Immunotherapy, 58: 1949-1957, (2009).
17. Han T H, Tang, Y C, Park Y H, Petersen L, Maynard J, Li P C, and Deisseroth A. Ad-sig-BcrAbl/ecdCD40L vector prime-BcrAbl/ecdCD40L protein boost vaccine for P210Bcr-Abl protein. Bone Marrow Transplantation, (2009).
18. Akbulut H, Tang Y, Akbulut K G, Maynard J, and Deisseroth A. Addition of adenoviral vector targeting of chemotherapy to the MUC-1/ecdCD40L VPPP vector prime protein boost vaccine prolongs survival of mice carrying growing subcutaneous deposits of Lewis lung cancer cells. Gene Therapy, 17: 1333-1340, (2010).
19. Deisseroth A, Tang Y, Zhang L, Akbulut H, and Habib N. TAA/ecdCD40L adenoviral prime-protein boost vaccine for cancer and infectious diseases. Cancer Gene Therapy advance online publication, 14 Dec. 2012; doi: 10.1038/cgt.2012.87.
20. Wu F, Zhao S, Yu B, Chen Y M, Wang W, Song Z G, Hu Y, Tao, Z W, Tian J H, Pel Y Y, Yuan M L, Zhang Y L, Dal F H, Liu Y, Wang Q M, Zheng J J, Xu, L Holmes E C and Zhang Y Z. A new coronavirus associated with human respiratory disease in China, Nature 579: 265-269, 2020.
21. Xia S, Yan L, Xu W, Afrawal A S, Algaissi A, Tseng C T K, Wang Q, Du L Y, dTan W, Wilson I A, Jiang S, Yang B, and Lu L. Aopann-coronavirus fusion inhibitor targeting the HIR1 domain of human coronavirus spike. Sci Adv 2019S: eaav4580, 2019.
22. Antibody resistance of SARS-CoV-2 Variants B.1.351 and B.1.1.7. Wang P, Nair M S S, Liu L H, Iketani S, Luo Y, Guo Y H, Wang M, Yu J, Zhang B S, Kwong P D, Grahan B S, Mascoala J R, Chang J Y, Yin M T, Sobieszczyk M, Kyratsous C A, Shappiro L, Sheng Z, Huang Y and Ho D D, Antibody resistance of Sars-CoV-2 variants B.1.351 and B.1.1.7. Nature https://doi.org/10.1038/s41586-021-03398-2 92021).
23. Sauer K and Harris T. An effective COVID-19 vaccine needs to engage T cells. Frontiers in Immunology 11:1-6, September 2020.
24. Dan J, Mateus J, Kato Y, Hastie K M, Yu E D, Faliti C E, Alba G, ramirez S I, Haupt S, Frazier A, Nakao C, Rayaprolu V, Rawlings S A, Peters B, Krammer F, Simon V, Saphire E O, Smith D M, Weiskopf D, Sette A, and Crotty S. Immunological memory to SARS-COV-2 assessed for up to 8 months after infection. Science 10.1126/sci
25. Editorial: EClinicalMedicine (2020) 100586, Editorial entitled: Understanding the Long-Term Health Effects of COVID-19. (Journal Home Page: https://www.jourals.elsevier.com/eclinicalmedicine

The invention claimed is:

1. An immunotherapeutic vaccine mixture for the SARS-CoV-2 virus with mutant variant strains, comprising multiple fusion proteins each having a distinct peptide, a first set of distinct peptides each from distinct domain regions from two domains of the S1 sub-unit of a Spike Protein of the SARS-CoV-2 virus, and a second set of distinct peptides each from one of of four functionally distinct domains of the S2 sub-unit of the Spike Protein of the SARS-CoV-2 virus, as a Target Associated Antigen (TAA), each TAA linked to the aminoterminal of the extracellular domain (ecd) of a CD40 ligand (CD40L), wherein each of said multiple ones of said peptides has at least one antigenic site for suppressing the evolution of multiple mutant variant strains of said virus, and wherein said TAA's comprise four or more of SEQ ID NOS 1-7.

2. An immunotherapeutic vaccine mixture for the SARS-CoV-2 virus according to claim 1, wherein each of said TAAs contains an amino acid fragment which binds to and is recognized by Class I MHC and Class II MHC for inducing neutralizing antibodies and activating dendritic cells, B cells and T cells.

3. An immunotherapeutic vaccine according to claim 2, wherein said TAAs comprise five or more of SEQ ID NOS 1-7.

4. An immunotherapeutic vaccine according to claim 2, wherein said TAAs comprise six or more of SEQ ID NOS 1-7.

5. An immunotherapeutic vaccine according to claim 2, wherein said TAAs comprise all seven of SEQ ID NOS 1-7.

6. An immunotherapeutic vaccine according to claim 2, wherein said vaccine mixture is encoded into a mRNA vaccine platform.

7. An immunotherapeutic composition for the SARS-CoV-2 virus with mutant variant strains, comprising a single mixture of multiple fusion proteins SEQ ID NOS 1-7, each having a distinct peptide from distinct and independent domains or domain regions from each of two subunits S1 and S2 of a Spike Protein of the SARS-CoV-2 virus as a Target Associated Antigen (TAA) linked to the aminoterminal of the extracellular domain (ecd) of a co-stimulatory molecule, wherein each of said multiple ones of said peptides has an antigenic site for suppressing the evolution of mutant variant strains of said virus and contains amino acid fragments which bind to and are recognized by Class I MHC and Class II MHC, for inducing neutralizing antibodies and activating dendritic cells, B cells and T cells, wherein said composition is encoded into a mRNA vaccine platform.

8. An immunotherapeutic composition for the SARS-CoV-2 virus according to claim 7, wherein the S2 sub-unit comprises four of said seven SEQ ID NOS 1-7, each of which four SEQ ID Nos 1-7 is from a different domain and is additionally functionally distinct one from the other.

9. An immunotherapeutic composition for the SARS-CoV-2 virus according to claim 7, wherein the SARS-CoV-2 virus forms a homotrimer, and the ecd of said co-stimulatory molecule forms a homotrimer, to stabilize biological interactions.

10. An immunotherapeutic composition for the SARS-CoV-2 virus according to claim 9, wherein said co-stimulatory molecule is the ecd of CD40L.

11. An immunotherapeutic regimen for the SARS-CoV-2 virus comprising seven fusion proteins, each of said fusion proteins comprising an extracellular domain (ecd) of the CD40L protein attached to mRNA encoding one of seven distinct Selected Fragments of the SARS-CoV-2 virus Spike Protein (SFSP) having two subunits S1 and S2, each one of said fragments representing a different functional feature of the Spike Protein or from a different domain or domain region of the Spike Protein, thereby generating seven SFSP/ecdCD40L distinct fusion proteins comprising SEQ ID NOS. 1-7.

12. An immunotherapeutic regimen according to claim 11, wherein each of said fusion proteins is adapted to induce a humoral and cellular immune response upon being administered to an individual.

13. An immunotherapeutic regimen according to claim, 12, wherein said seven fusion proteins are combined into a single mixture.

14. An immunotherapeutic regimen according to claim 13, wherein said regimen has the capability to suppress the emergence of multiple immunological escape mutants.

15. An immunotherapeutic regimen according to claim 11, wherein each of SEQ ID NOS. 1-3 is from different domain region of the Spike Protein S1 subunit, and each of SEQ ID NOS. 4-7 is from a different one of four domains of the of the Spike Protein S2 subunit where each of the S2 subunit four domains has a different function.

\* \* \* \* \*

SEQUENCE LISTING

<160> NUMBER OF SEQ ID NOS: 7

<210> SEQ ID NO 1
<211> LENGTH: 54
<212> TYPE: PRT
<213> ORGANISM: Artificial Sequence
<220> FEATURE:
<223> OTHER INFORMATION: Synthetic Construct

<400> SEQUENCE: 1

Val Arg Phe Pro Asn Ile Thr Asn Leu Cys Pro Phe Gly Glu Val Phe
1 5 10 15

Asn Ala Thr Arg Phe Ala Ser Val Tyr Ala Trp Asn Arg Lys Arg Ile
20 25 30

Ser Asn Gly Val Ala Asp Tyr Ser Val Leu Tyr Asn Ser Ala Ser Phe
35 40 45

Ser Thr Phe Lys Cys Tyr
50

<210> SEQ ID NO 2
<211> LENGTH: 61
<212> TYPE: PRT
<213> ORGANISM: Artificial Sequence
<220> FEATURE:
<223> OTHER INFORMATION: Synthetic Construct

<400> SEQUENCE: 2

Gly Val Ser Arg Thr Lys Leu Asn Cys Leu Cys Phe Thr Asn Val Tyr
1 5 10 15

Ala Asp Ser Phe Val Ile Arg Gly Asp Glu Val Arg Gln Ile Ala Pro
20 25 30

Gly Gln Thr Cys Lys Ile Ala Asp Tyr Asn Tyr Lys Leu Pro Asp Asp
35 40 45

Phe Thr Gly Cys Val Ile Ala Trp Asn Ser Asn Asn Leu
50 55 60

<210> SEQ ID NO 3
<211> LENGTH: 40

```
<212> TYPE: PRT
<213> ORGANISM: Artificial Sequence
<220> FEATURE:
<223> OTHER INFORMATION: Synthetic Construct

<400> SEQUENCE: 3

Ser Phe Ile Glu Asp Leu Leu Phe Asn Lys Val Thr Leu Ala Asp Ala
1               5                   10                  15

Gly Phe Ile Lys Gln Tyr Gly Asp Cys Leu Gly Asp Ile Ala Ala Arg
            20                  25                  30

Asp Leu Ile Cys Ala Gln Lys Arg
        35                  40

<210> SEQ ID NO 4
<211> LENGTH: 40
<212> TYPE: PRT
<213> ORGANISM: Artificial Sequence
<220> FEATURE:
<223> OTHER INFORMATION: Synthetic Construct

<400> SEQUENCE: 4

Ser Phe Ile Glu Asp Leu Leu Phe Asn Lys Val Thr Leu Ala Asp Ala
1               5                   10                  15

Gly Phe Ile Lys Gln Tyr Gly Asp Cys Leu Gly Asp Ile Ala Ala Arg
            20                  25                  30

Asp Leu Ile Cys Ala Gln Lys Arg
        35                  40

<210> SEQ ID NO 5
<211> LENGTH: 29
<212> TYPE: PRT
<213> ORGANISM: Artificial Sequence
<220> FEATURE:
<223> OTHER INFORMATION: Synthetic Construct

<400> SEQUENCE: 5

Asp Ile Ser Gly Ile Asn Ala Ser Val Val Asn Ile Gln Lys Glu Ile
1               5                   10                  15

Asp Arg Leu Asn Glu Ser Leu Ile Asp Leu Gln Glu Leu
            20                  25

<210> SEQ ID NO 6
<211> LENGTH: 37
<212> TYPE: PRT
<213> ORGANISM: Artificial Sequence
<220> FEATURE:
<223> OTHER INFORMATION: Synthetic Construct

<400> SEQUENCE: 6

Leu Gly Phe Ile Ala Gly Leu Ile Ala Ile Val Met Val Thr Ile Met
1               5                   10                  15

Leu Cys Cys Met Thr Ser Cys Cys Ser Cys Leu Lys Gly Cys Cys Ser
            20                  25                  30

Cys Gly Ser Cys Cys
        35

<210> SEQ ID NO 7
<211> LENGTH: 40
<212> TYPE: PRT
<213> ORGANISM: Artificial Sequence
<220> FEATURE:
<223> OTHER INFORMATION: Synthetic Construct
```

```
<400> SEQUENCE: 7

Leu Cys Cys Met Thr Ser Cys Cys Ser Cys Leu Lys Gly Cys Cys Ser
1               5                   10                  15

Cys Gly Ser Cys Cys Lys Phe Asp Glu Asp Ser Glu Pro Val Leu
            20              25                  30

Lys Gly Val Lys Leu His Tyr Thr
        35              40
```